United States Patent [19]

Kingsley et al.

[11] Patent Number: 5,994,567
[45] Date of Patent: Nov. 30, 1999

[54] DIRECT OXYGEN INJECTION INTO BUBBLE COLUMN REACTORS

[75] Inventors: Jeffrey Paul Kingsley, East Amherst, N.Y.; Roger William Day, Southbury, Conn.; Lawrence Marvin Litz, Pleasantville, N.Y.

[73] Assignee: Praxair Technology, Inc., Danbury, Conn.

[21] Appl. No.: 09/128,746

[22] Filed: Aug. 4, 1998

Related U.S. Application Data

[63] Continuation of application No. 08/766,603, Dec. 12, 1996, abandoned.

[51] Int. Cl.$^6$ .................................................. F27B 15/08
[52] U.S. Cl. .................................................. 552/208
[58] Field of Search ..................... 568/569, 357, 568/836, 565; 562/412, 536; 560/204; 422/145; 552/208

[56] References Cited

U.S. PATENT DOCUMENTS

| | | | |
|---|---|---|---|
| 3,054,814 | 9/1962 | Jason et al. | 260/413 |
| 4,001,090 | 1/1977 | Kalina | 195/109 |
| 4,491,674 | 1/1985 | Rieber et al. | 568/357 |
| 4,782,024 | 11/1988 | Scott et al. | 435/247 |
| 4,867,918 | 9/1989 | Kiyonaga et al. | 261/76 |
| 5,277,878 | 1/1994 | Piotrowski et al. | 422/129 |
| 5,356,600 | 10/1994 | Kiyonago et al. | 422/234 |
| 5,523,474 | 6/1996 | Kingsley et al. | 562/416 |
| 5,536,875 | 7/1996 | Roby et al. | 562/412 |

FOREIGN PATENT DOCUMENTS

WO96/31442 10/1996 WIPO.

OTHER PUBLICATIONS

Gehard Franz, Roger A. Sheldon "Oxidation", *Ullmann's Encyclopedia of Industrial Chemistry*, vol. A18, pp. 62–311.

Roffla et al, "Byproduct Indentification in the Terephthalic Acid Production Process and Possible Mechanisms of Their Formation", *Ind. Eng. Chem. Prod. Res. Dev. 1984*, 23, 629–634.

H.F. Svendsen et al., "Local Flow Structures in Internal Loop and Bubble Column Reactors", *Chemical Engineering Science*, vol. 47, No. 13/14, pp. 3297–3304, 1992.

*Primary Examiner*—Jose' G. Dees
*Assistant Examiner*—Alton Pryor
*Attorney, Agent, or Firm*—Robert J. Follett

[57] ABSTRACT

The invention is directed to a liquid phase oxidation process, wherein a first oxygen-containing gas is injected into the lower portion of a bubble column reactor vessel containing an oxidizeable organic liquid. A second oxygen-containing gas is further injected into the reactor at a point or points wherein the liquid is substantially depleted in dissolved oxygen prior to said injection. Oxygen from both the first and second oxygen-containing gases is used to oxidize the organic liquid.

14 Claims, 4 Drawing Sheets

DIRECT OXYGEN INJECTION INTO BUBBLE COLUMN REACTORS

This is a Continuation of prior U.S. application Ser. No. 08/766,603 Filing Date: Dec. 12, 1996, now abandoned.

FIELD OF THE INVENTION

This invention is directed towards air-based oxidation reactions which take place in bubble column reactors. In particular, the invention is directed towards improving both product quality and reactor performance characteristics, including product yield, oxygen utilization and productivity, in such reactions by direct injection of oxygen into the reactors.

BACKGROUND

Bubble column reactors (BCRs) are widely-used in the chemical industry as a low-maintenance, inexpensive means to mix and react gases with liquids, particularly in liquid phase oxidations of organic chemicals. In such liquid phase oxidations most, if not all, of the oxidation reaction occurs with oxygen dissolved in the liquid rather than the oxygen in the gas bubble. Therefore, the rate of oxygen dissolution is generally a prime factor in the process.

In its simplest form, a BCR as used for liquid phase oxidations is comprised of a column of liquid into the bottom quarter of which a reactant gas such as air or oxygen enriched air (e.g. air having up to 40 vol. % oxygen) is injected. The buoyancy of the injected gas causes the bubbles to flow upward. This upward flow of gas bubbles pulls surrounding liquid upward. The amount of liquid which flows upward due to bubble buoyancy exceeds the net liquid flow through the column. Therefore, the upward flow of liquid in regions where many or large bubbles exist must be countered by the downward flow of liquid in regions where such bubbles are rare. In this way, a liquid circulation pattern is created which is unique to the specific geometry of the BCR. Since BCRs have no mechanical agitation, the injected reactant gas functions to mix the liquid.

Most liquid phase oxidations of organic chemicals occur via free radical chain mechanisms. In general, the mechanism proceeds by four steps: initiation, propagation, branching, and termination. The termination of the radical chain involves the combination of free radicals. High molecular weight by-products are produced in termination reactions because two radicals react with each other prior to reacting with oxygen. The normal termination reactions are as follows:

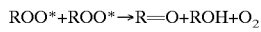  1)

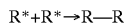  2)

In the above reactions ROO* are peroxide radicals and R* are hydrocarbon radicals. In the presence of sufficient oxygen, the concentration of ROO* radicals is relatively high and the reaction of two ROO* radicals in reaction 1 dominates. However, if there is insufficient oxygen, as in an oxygen-starved region of a reactor, the reaction of the two radicals in reaction 2 will become significant, thus forming undesirable high molecular weight by-products. In addition to forming these by-products, the recombinations will enhance the termination rate over the propagation rate, consequently lowering the overall reaction rate.

The high molecular weight by-products are typically colored and difficult to remove from the final product. As such, they may devalue the product, even at very low concentrations. Thus the elimination of the radical pathway of reaction 2 can substantially increase product value and, in some cases, may also significantly increase reaction selectivity.

In reactors of this type the use of air enriched with up to 40% oxygen has been employed to increase production rates. However, the use of oxygen enriched air can create regions of the reactor having undesirably high reaction rates, and often undesired, excessively high, temperatures. Indeed this is often a problem for air fed reactors generally. Unfortunately, these high temperatures may promote the formation of byproducts such as carbon oxides in these regions, and as such the yield of the desired product and/or the productivity of the reactor is reduced.

Another problem with BCRs is that because of the flow patterns established, gas is not uniformly distributed in the liquid. Further, in the air-based oxidation of organic chemicals, oxygen-depleted air bubbles dominate large portions of the reactor. Coalescence of both these bubbles and feed air and/or enriched air bubbles leads to the formation of plumes of large bubbles which, due to their size, are very inefficient in transferring oxygen. Thus, even though oxygen may appear in the waste gas stream, the reaction may, in fact, be oxygen-deficient. In practice, due to inefficient mass transfer, only about 80% of the oxygen provided in either air or oxygen enriched air is typically utilized in the oxidations. Unfortunately, the remaining oxygen collects in the headspace of the reactor and may create an explosion hazard.

In some BCR systems, the regions where feed air or enriched air reacts are intentionally kept at an excessive temperature in order to ensure reaction prior to coalescence of the feed bubbles. The reason for such operation is to promote oxidation and keep the oxygen concentration in the waste gas stream below the explosive limit. Unfortunately, operation at such temperatures also may promote the formation of undesirable byproducts, such as carbon oxides in these regions, and the yield of the desired product and/or the productivity of the reactor is reduced. We should note that by the term "explosive limit" we mean the oxygen concentration at which the gas stream could be subject to explosion. Such limits differ depending upon reactant and process conditions, but are known to those skilled in the art.

Other practitioners have attempted to redistribute the gas feed at several stages in the reactor by breaking up coalesced bubbles such that the surface area for oxygen mass transfer is increased. Methods for redistribution include the use of perforated trays and/or packing materials. Each of these options has some disadvantages. For example, in addition to adding complexity to the reactor, they also add metal surface area. In most radical reactions, this is undesirable since undesired radical recombination is promoted at metal surfaces. Also, the presence of hardware in the reactor will substantially alter the circulation pattern and may actually reduce reactor productivity. Thus there is a need in the art to provide a simplified, more efficient method for preventing the formation of byproducts in BCRs.

OBJECTS OF THE INVENTION

It is therefore an object of the invention to provide a process for liquid phase oxidations in bubble column reactors whereby the formation of byproducts is reduced.

It is a further object of the invention to provide a process for liquid phase oxidations in bubble column reactors whereby the formation of byproducts is reduced while reactor productivity is maintained or increased.

SUMMARY OF THE INVENTION

The above and other objects, which will become apparent to one skilled in the art upon a reading of this disclosure, are attained by the present invention, one aspect of which is:

A liquid phase oxidation process, said process comprising:

a) providing a reactor vessel containing an organic liquid capable of undergoing oxidation;

b) injecting a first oxygen-containing gas into the bottom portion of said vessel, such that bubbles of said first oxygen containing gas flow upwardly through said vessel to cause an upward flow of said organic liquid; and c) injecting a second oxygen-containing gas into said reactor at at least one point within said organic liquid wherein there is a deficiency of dissolved oxygen.

Another aspect of the invention is an apparatus for carrying out a liquid phase oxidation wherein the apparatus comprises:

a) a reactor vessel comprising an organic liquid capable of being oxidized;

b) a first injector communicating with the interior of the reactor vessel for injecting a first oxygen-containing gas into the reactor vessel for passage through said reactor vessel; and c) at least one additional injector positioned such that a second oxygen-containing gas is introduced into said reactor vessel at at least one point within said organic liquid having a deficiency of dissolved oxygen.

As used herein the term "bottom portion" means the lower quarter of the reactor vessel.

BRIEF DESCRIPTION OF THE DRAWINGS

Other objects, features and advantages will occur to those skilled in the art from the following description of preferred embodiments and the accompanying drawings, in which.

DETAILED DESCRIPTION OF THE INVENTION

Figure 1:
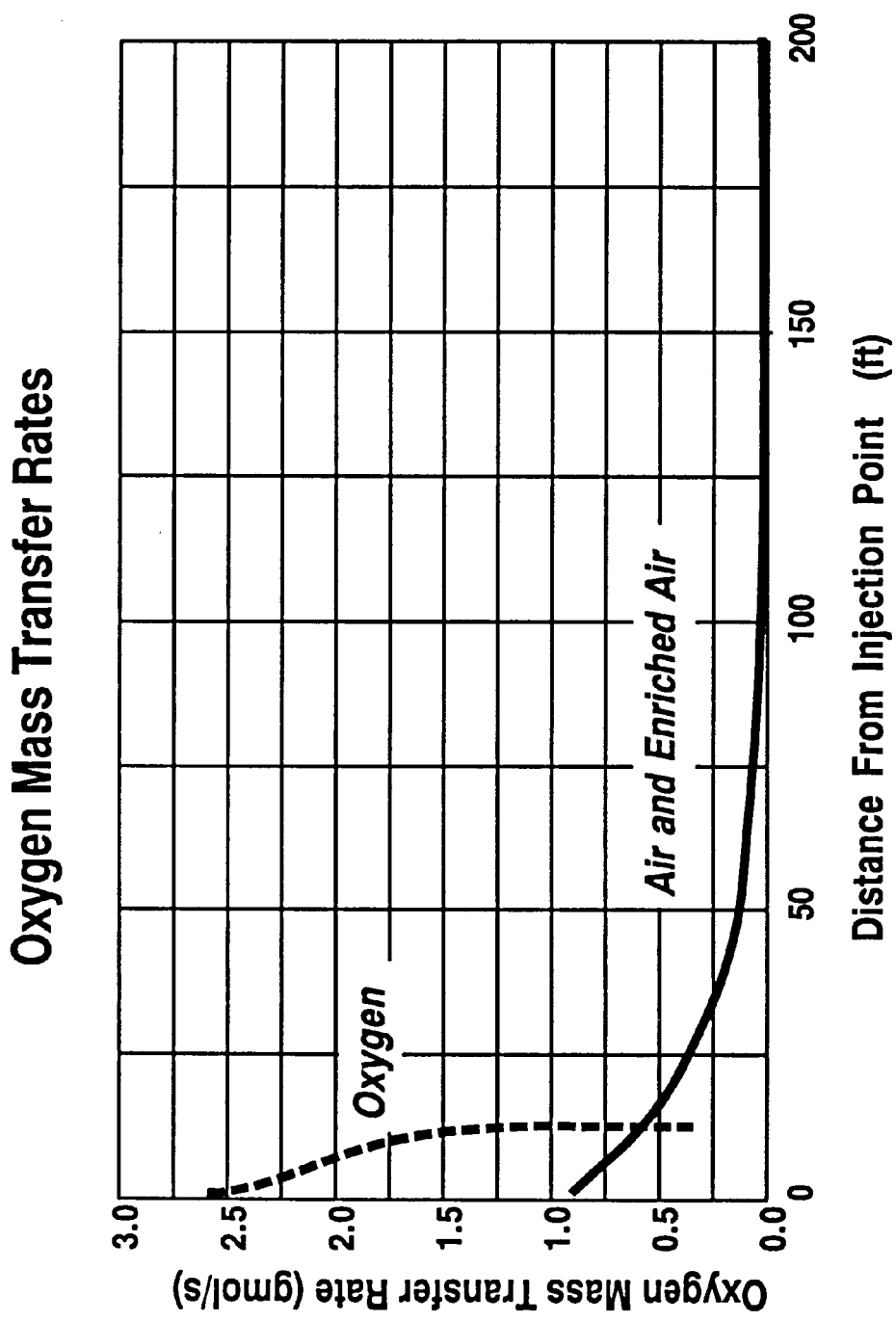
FIG. 1 is a graph showing the comparative rate of mass transfer (or dissolution) of oxygen from air and oxygen bubbles into the liquid as derived by modeling.

Our modeling has shown that the mass transfer of oxygen from oxygen bubbles into the liquid is significantly faster than from air bubbles or air bubbles enriched with oxygen. This is illustrated in FIG. 1, which shows the predictions of our model of oxygen mass transfer from a bubble into an organic liquid.

In this model, the same total amount of oxygen is added to the liquid either via pure oxygen bubbles, oxygen enriched (25 vol. %) air bubbles, or air (21 vol. % oxygen). The rate of oxygen mass transfer from an oxygen bubble is compared to the rate of oxygen mass transfer from air bubbles or air bubbles enriched to 25% oxygen. Due to the presence of inert nitrogen, the concentration of oxygen in the air bubbles and enriched air bubbles diminishes as oxygen is transferred out of the bubble.

In contrast, the concentration of oxygen in the oxygen bubble remains constant, and any diminution of oxygen transfer rate is due solely to the decrease in the available area due to shrinkage of the bubble. This model assumes that the oxygen, air and enriched air bubbles all begin at the same size, and that there is no coalescence of bubbles and no evaporation of solvent into the bubble.

In actual practice, the effects of solvent evaporation on mass transfer can be significant. In addition, air and enriched air bubbles are subject to significant coalescence because, due to the presence of large concentrations of nitrogen, they persist from the point of injection until they escape through the upper surface of the liquid and they also expand in volume as they rise through the liquid due to decrease in hydrostatic pressure. For example, through proper injector design, a typical size for an injected oxygen bubble may be one millimeter. Significantly for this application, the oxygen in these bubbles dissolves so quickly that there is little or no coalescence. In contrast, air bubbles coalesce and can grow to be up to 5 cm or larger. Our modeling has shown that the range of the oxygen mass transfer rates is a full two orders of magnitude smaller with the air or enriched air bubbles as compared to pure oxygen. For those reactions that are limited by mass transfer rate of oxygen, the increase in mass transfer rate associated with these small oxygen bubbles can generate higher rates of chemical reaction.

The invention will be discussed in detail with reference to FIGS. 2–4a. In these Figures the reference numbers are the same for common elements. Computational fluid dynamics (CFD) modeling shows that for a typical BCR, where reactant gas is injected into the bottom portion of the reactor, two possible flow patterns emerge. The first is shown in FIG. 2.

Figures 2, 2A:
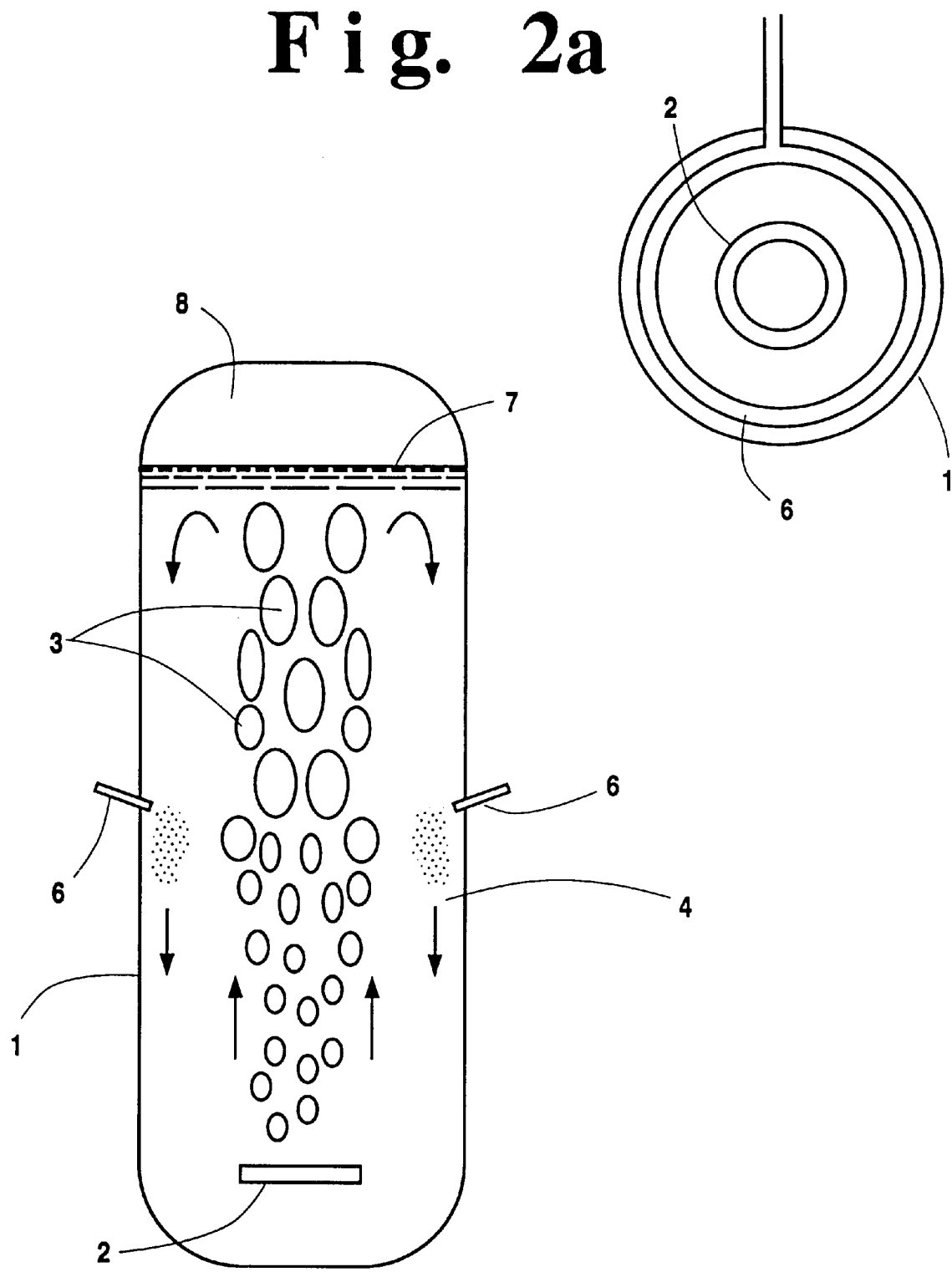
FIG. 2 is a cross-sectional elevation view of one embodiment of the invention.
FIG. 2a is a cross-sectional top-down view of one embodiment of the invention.

FIG. 2 shows a reactor vessel 1 which contains an organic liquid capable of being oxidized. For the purposes of the invention, reactor vessel 1 typically has an aspect ratio (height over diameter) of between 6 and 8. However, reactor vessels having an aspect ratio as small as 2 or larger than 10 are also contemplated.

The organic liquids may include, but are not limited to, cumene which is oxidized to form cumenehydroperoxide, cyclohexane which is oxidized to form a mixture of cyclohexanone and cyclohexanol, p-xylene which is oxidized in a process to produce dimethylterephthalate or terephthalic acid, anthrahydroquinone which is oxidized to form a peroxyanthraquinone, which is a precursor to hydrogen peroxide, and acetaldehyde which is oxidized to form acetic acid.

In a typical BCR, if a first oxygen-containing gas, which is either air or oxygen enriched air (having an oxygen content of up to 40 vol. %), is injected in the bottom portion of the reactor vessel 1 near the center of the reactor diameter through injector 2, it will coalesce into bubbles 3 having diameters of up to 5 cm or larger, within one or two reactor diameters. The central portion of the reactor will be heavily loaded with gas having a net upward flow. This flow will cause the organic liquid reactant to rise within the vessel 1, as depicted by the upwardly pointing arrows. As the upwardly flowing reactant approaches the top of vessel 1, it changes course and flows down vessel 1, as shown by the downwardly pointing arrows, in a recirculating pattern. Because the gas contained in the bubbles is released into the head space at the top of the reactor, region 4 near the walls of the vessel 1 will have a net downflow of liquid with little or no gas present and, as the reaction continues between the dissolved oxygen and organic liquid, the liquid will become essentially oxygen depleted. It is in this region (4), of insufficient dissolved oxygen, that a second oxygen-containing gas, having an oxygen content of at least 70 vol. %, more preferably at least 90 vol. % oxygen, will be injected into the reactor through at least one injection nozzle 6. Below the lower limit of less than 70 vol. %, too much inert nitrogen may be introduced into the process, thus altering the flow patterns of the reactor. In an alternative embodiment, as shown in FIG. 2a, the oxygen injector may be a tubular ring 6 having several orifices or nozzles therein which is within the circumference of the reactor 1.

Figures 3, 3A:
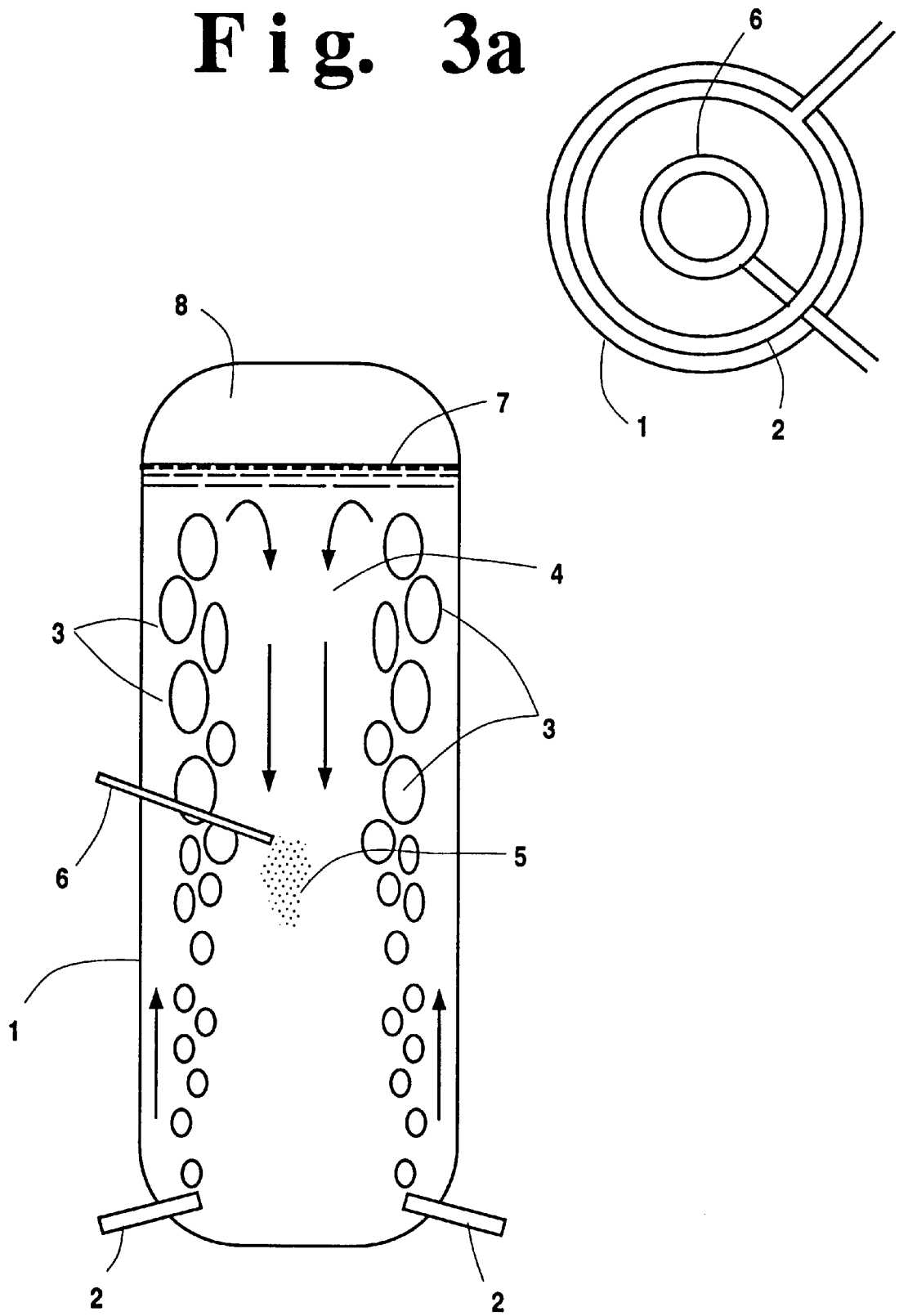
FIG. 3 is a cross-sectional elevation view of one embodiment of the invention.
FIG. 3a is a cross-sectional top-down view of one embodiment of the invention.

As shown in FIG. 3, if the first oxygen-containing gas is injected into the bottom portion of the vessel 1 near the walls through injector 2, it will tend to hug the walls, again coalescing into large slugs of gas 3. The organic liquid near the walls will tend to flow upwardly, as shown by the arrows, while the liquid in the center of the reactor will have a net downflow as shown by the arrows. Again, gas in the bubbles will release into the head space of the reactor, and consequently the central core 5 of the vessel 1 will tend to have little or no gas and will become essentially oxygen depleted. It is into this region that the second-oxygen containing gas will be injected into the vessel through at least one injection nozzle 6. In an alternative embodiment, as shown in FIG. 3a, the oxygen injector may be a tubular ring 6 having several orifices or nozzles therein which is within the circumference of the reactor 1.

As suggested above, the regions which are essentially depleted of dissolved oxygen are typically found in the portions of the of the reactor where there is a net downflow of liquid. The existence of regions with insufficient dissolved oxygen can be determined from the presence of undesirable high molecular weight byproducts which are formed in the absence of oxygen. Flow models (both experimental and computer-based) may be used to determine the optimal location for oxygen injection.

The precise location of these downflow regions is sensitive to the reactor geometry, the presence of internal baffles and heat transfer surfaces, and the injector geometry, but would be recognized by those of ordinary skill in the art.

As discussed, these regions will not have any significant oxygen mass transfer to them and, in typical reactor systems, will generally be essentially oxygen-depleted. As such, any oxygen bubbles from said second oxygen-containing gas which is injected in these locations will be rapidly dissolved. These oxygen bubbles will have a very small diameter (on the order of 1 mm) as compared to the bubbles of said first oxygen-containing gas and, therefore, little buoyancy. Since they are consumed rapidly, there will be little opportunity for the oxygen bubbles to coalesce and become buoyant. Therefore, they will not affect the general reactor hydrodynamics.

Those skilled in the art will appreciate that the amount of oxygen employed in any particular oxidation, relative to the amount of oxygen added in the air or oxygen-enriched air feed, will vary depending on the particular features of the oxidation, such as the particular liquid involved, the operating conditions pertaining to the oxidation, and the like. Thus the amount of oxygen added through the second oxygen-containing gas may be greater than or less than the amount of oxygen added from the first oxygen-containing gas.

Total replacement of air with oxygen is not readily accomplished in existing BCRs due in part to explosion hazards associated with high oxygen concentrations in the reactor head space. Another reason for not replacing air with oxygen is that the inert nitrogen in air provides the buoyancy induced stirring that acts to mix the liquid in the vessel.

Figures 4, 4A:
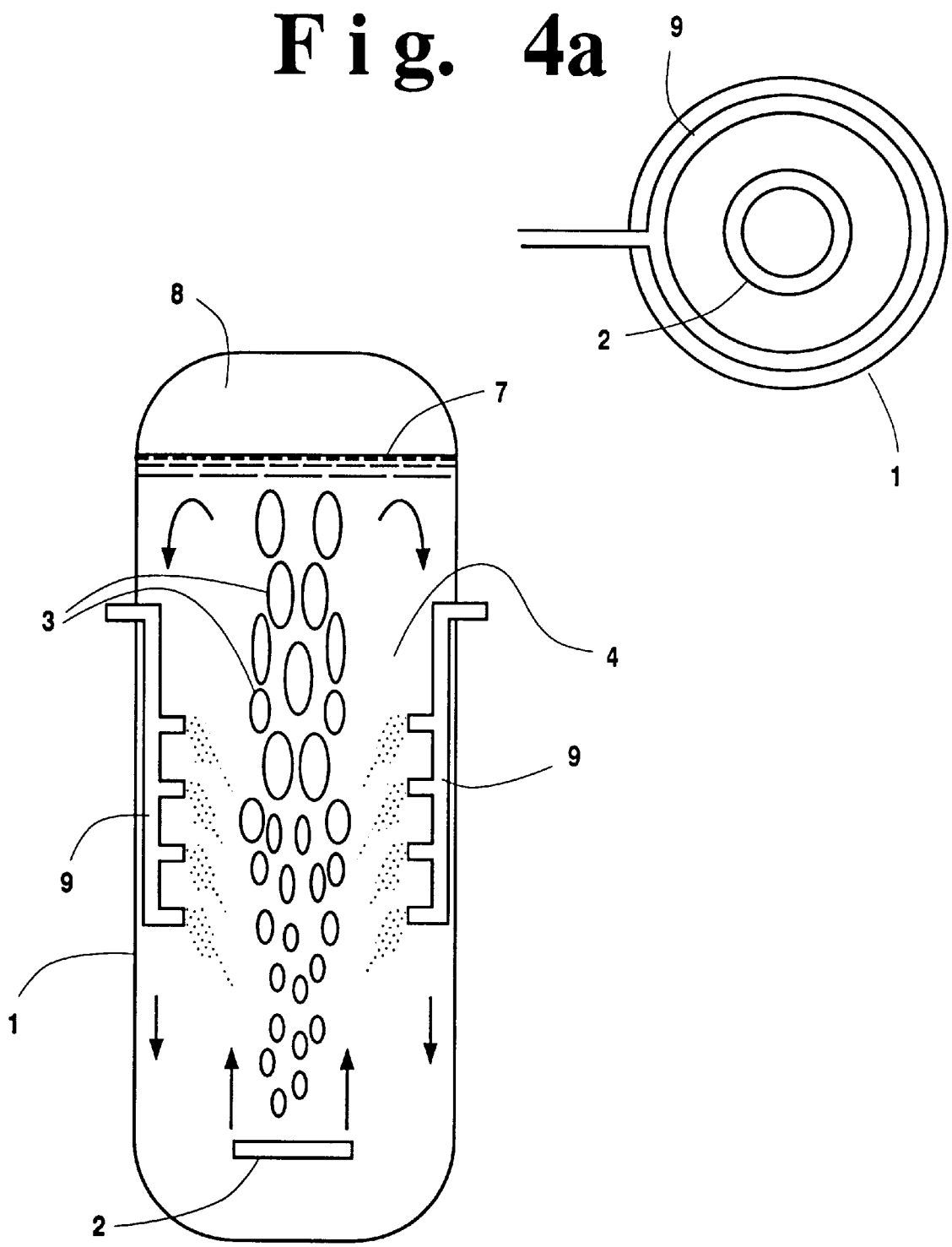
FIG. 4 is a cross-sectional elevation view of a one embodiment of the invention.
FIG. 4a is a cross-sectional top-down view of one embodiment of the invention.

An alternative embodiment of the invention would include multiple injection points of oxygen. Because BCRs tend to have a large length to diameter ratio, there may be several locations along the downflow where the liquid may be depleted of oxygen. In such an embodiment, injector 9 would be used as shown in FIG. 4 to inject said second oxygen-containing gas. In an alternative embodiment, the oxygen injector may comprised of a series of tubular rings 9 having several orifices or nozzles therein which are within the circumference of the reactor 1.

The invention offers several benefits. For example, due to the improved mass transfer associated with the injection of the second oxygen containing gas, up to 100% of this gas that is introduced may be utilized. As such the process of the invention offers improved efficiencies and cost advantages over conventional enrichment processes in which, as discussed above, oxygen utilization is typically about 80%. In addition, because up to 100% of the added oxygen may be utilized, explosion hazards associated with excess oxygen in the headspace of the reactor are determined primarily by the residual oxygen in the air or oxygen enriched air bubbles rising out of the surface of the liquid.

As may be inferred from the above discussion, by promoting the reaction of radicals in the regions identified above, the formation of undesirable coupled by-products is suppressed. Consequently, because reactants, which in the absence of oxygen would react to form undesirable by-products, are oxidized, improved product yields and higher purity products are obtained.

In addition, because there is little or no additional inert gas present, the overall circulation pattern of the reactor is not substantially disrupted by the presence of additional inert gas bubbles. In contrast, the staged injection of air into these downflow regions will change circulation patterns because the high nitrogen content in air will tend to drive bubbles upward against the flow. This would lead to undesirable consequences such as poor liquid circulation patterns in the reactor, and consequently inefficient heat transfer.

Still another benefit of the process is related to the productivity of the reactor. Regions of the reactor which were previously unused (because they contained insufficient oxygen to support reaction) may now be used due to the process of this invention.

Further, the invention is applicable to those reactors having excessive carbon oxide byproduct formation due to the presence of high temperature regions where air or enriched air is fed. In such situations, it may be desirable to improve the yield of the preferred product and/or the productivity of the reactor by reducing the primary input of air or of enriched air so as to reduce the liquid temperature in this region. The productivity (e.g. amount of desired reaction product) lost in these regions can be compensated for, or exceeded, by gains in product yield and reactor productivity in the regions where the second oxygen containing gas is added in accordance with this invention.

The invention is also applicable to those reactors where the temperature of the air/enriched air reaction regions has been intentionally kept high in order to keep the oxygen in the waste gas stream below the explosive level. Such high temperatures often lead to the formation of undesirable by-products such as carbon oxides, which reduce the potential yield. Through the process of the invention, the flow of the air/enriched air may be reduced to a point wherein the oxygen concentration in the waste stream would be below the explosive level or limit at a lower, preferred temperature. The productivity (e.g. amount of desired reaction product) lost in these regions can be compensated for, or exceeded, by gains in product yield and/or reactor productivity in the regions where the second oxygen containing gas is added in accordance with this invention.

Finally, this technology provides the additional economic benefit of reducing the amount of air compression energy required per unit of product. This is because the invention allows one to increase reactor production without having to increase the amount of compressed feed air. By extrapolation of this reasoning, one may maintain the amount of reactor production, and decrease the amount of feed air.

Specific features of the invention are shown in one or more of the drawings for convenience only, as each feature may be combined with other features in accordance with the invention. Alternative embodiments will be recognized by those skilled in the art and are intended to be included within the scope of the claims.

What is claimed is:

1. A liquid phase oxidation process, said process comprising:
   a) providing a reactor vessel containing an organic liquid capable of undergoing oxidation;
   b) injecting a first oxygen-containing gas into a lower portion of said reactor vessel, such that bubbles of said first oxygen containing gas flow upwardly through said reactor vessel to cause an upward flow of said organic liquid and such that oxygen dissolves into said organic liquid; and
   c) injecting a second oxygen-containing gas into said reactor vessel at at least one point within said organic liquid wherein there is a deficiency of dissolved oxygen, wherein said injection of a first oxygen containing gas creates a circulation pattern in said reactor vessel, and said pattern promotes mixing of said organic liquid, and wherein said second oxygen containing gas is injected in that said second oxygen containing gas has substantially no effect upon said circulation pattern, and wherein said reactor vessel is a bubble column reactor having no mechanical agitation means therein.

2. The process according to claim 1, wherein said first oxygen-containing gas is air.

3. The process according to claim 1, wherein said first oxygen-containing gas is oxygen enriched air.

4. The process according to claim 1, wherein said second oxygen-containing gas is oxygen having a purity of at least 90 vol. %.

5. The process according to claim 1, wherein yield of the oxidation process is increased as compared to a process wherein said second oxygen-containing gas is not added to the reactor vessel.

6. The process according to claim 1, wherein oxygen utilization in the reactor vessel is increased as compared to a process wherein said second oxygen-containing gas is not added to the reactor vessel.

7. The process according to claim 1, wherein said second oxygen containing gas is added in an amount effective to allow for a reduction in the amount of said first oxygen containing gas, such that the amount of oxidation product produced in said oxidation process is at least as great as compared to a process wherein said second oxygen-containing gas is not added to the reactor vessel.

8. The process according to claim 1, wherein production of carbon oxide byproducts is substantially reduced in said liquid phase oxidation process as compared to a process wherein said second oxygen-containing gas is not added to the reactor vessel.

9. The process according to claim 7, wherein production of carbon oxide byproducts is substantially reduced in said liquid phase oxidation process as compared to a process wherein said second oxygen-containing gas is not added to the reactor vessel.

10. The process according to claim 1, wherein the reactor vessel contains a headspace above said organic liquid wherein unreacted and reaction byproduct gases accumulate during said oxidation process, and wherein the amount of oxygen in said headspace is in a concentration below the explosive limit.

11. The process according to claim 7, wherein the reactor vessel contains a headspace above said organic liquid wherein unreacted and reaction byproduct gases accumulate during said oxidation process, and wherein the amount of oxygen in said headspace is in a concentration below the explosive limit.

12. The process according to claim 9, wherein the reactor vessel contains a headspace above said organic liquid wherein unreacted and reaction byproduct gases accumulate during said oxidation process, and wherein the amount of oxygen in said headspace is in a concentration below the explosive limit.

13. The process according to claim 1, wherein said organic liquid is selected from the group consisting of cumene, cyclohexane, p-xylene, anthrahydroquinone and acetaldehyde.

14. A liquid phase oxidation process, said process comprising:
   providing a reactor vessel containing an organic liquid capable of undergoing oxidation;
   b) injecting a first oxygen-containing gas into a lower portion of said reactor vessel, such that bubbles of said first oxygen containing gas flow upwardly through said reactor vessel to cause an upward flow of said organic liquid and such that oxygen dissolves into said organic liquid; then
   c) locating at least one point within said reactor vessel wherein the liquid is substantially depleted in dissolved oxygen;
   d) injecting a second oxygen-containing gas into said reactor vessel at said point or points wherein the liquid is substantially depleted in dissolved oxygen, wherein said injection of said first oxygen containing gas creates a circulation pattern in said reactor vessel, and said pattern promotes mixing of said organic liquid, and wherein said second oxygen containing gas is injected in that second oxygen containing gas has substantially no effect upon said circulation pattern, and wherein said reactor vessel is a bubble column reactor having no mechanical agitation means therein.

* * * * *